United States Patent
Kostenis et al.

(10) Patent No.: US 7,348,155 B2
(45) Date of Patent: Mar. 25, 2008

(54) METHOD FOR IDENTIFYING COMPOUNDS FOR TREATING AGING PROCESSES IN THE CORONARY CIRCULATORY SYSTEM

(75) Inventors: Evi Kostenis, Frankfurt am Main (DE); Andreas Busch, Kelkheim (DE); Vera Regitz-Zagrosek, Berlin (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 544 days.

(21) Appl. No.: 10/166,841

(22) Filed: Jun. 11, 2002

(65) Prior Publication Data

US 2003/0100484 A1    May 29, 2003

(30) Foreign Application Priority Data

Jun. 29, 2001  (DE)  ............... 101 31 458

(51) Int. Cl.
- *G01N 33/567* (2006.01)
- *C12Q 1/68* (2006.01)
- *C12P 21/06* (2006.01)
- *A61K 38/04* (2006.01)
- *C07K 17/00* (2006.01)

(52) U.S. Cl. .................. 435/7.21; 435/6; 435/69.1; 530/327; 530/326

(58) Field of Classification Search .............. None
See application file for complete search history.

(56) References Cited

FOREIGN PATENT DOCUMENTS

| WO | WO99/40192  | 8/1999  |
| WO | WO00/75168  | 12/2000 |
| WO | WO 01/14888 | 3/2001  |

OTHER PUBLICATIONS

Cotran, et al. Editors. Robbins Pathologic Basis of Disease, 6th edition, 1999, pp. 544.*
Alberts, et al. 2002. Molecular Biology of the Cell. 4th edition, pp. 1090-1091.*
Douglas SA and Ohlstein EH. 2000. Trends Cardiovasc Med. 10:229-237.*
Liu et al., 1999. World J Gastroenterology 6:361-364.*
Tzanidis et al. 2000. European Heart J. 21 Supp [S]:72 (p. 516).*
Deten et al. 2001. J Mol Cell Cardiol 33:1191-1207.*
Ghosh 2002. Exp Biol Med 227:301-314.*
M. Neuss et al., Isolation and Characterization of Human Cardiac Fibroblasts From Explanted Adult Hearts, Cell & Tissue Research, vol. 286, 1996, pp. 145-153.
A. Tzanidis et al., Urotensin II Stimulates Collagen Synthesis By Cardiac Fibroblasts And Hypertrophic Signalling In Cardiomyocytes Via G(alpha)q- and Ras-dependent Pathways, Journ. of American College of Cardiology, vol. 37, No. 2, Feb. 2001, p. 164A.
Fitzgerald et al., Matrix metalloproteinases can facilitate the heparanase-induced promotion of phenotypic chane in vascular smooth muscle cells, Atherosclerosis, vol. 145, No. 1, Jul. 1999, pp. 97-106.
Chen et al., CTGF Expression is Induced by TGF-Beta in Cardiac Fibroblasts and Cardiac Myocytes: a Potential Role in Heart Fibrosis, Journ. of Molecular and Celluclar Cardiology, vol. 32, No. 10, Oct. 2000, pp. 1805-1819.
Douglas et al., Human Urotension-II, the Most Potent Mammalian Vasconstrictor Identified To Date, as a Therapeutic Target for the Management of Cardiovascular Disease, Trends in Cardiovascular Medicine, vol. 10, No. 6, Aug. 2000, pp. 229-237.

* cited by examiner

*Primary Examiner*—Manjunath Rao
*Assistant Examiner*—Shulamith H Shafer

(57) ABSTRACT

The invention relates to a method for identifying a compound which modifies the activity of the urotensin II receptor, with genes or gene products which are involved in the structure, formation or breakdown of the extracellular matrix being influenced.

8 Claims, No Drawings

METHOD FOR IDENTIFYING COMPOUNDS FOR TREATING AGING PROCESSES IN THE CORONARY CIRCULATORY SYSTEM

PRIORITY CLAIM

This application claims the benefit of German Patent Application Number DE 101 31 458.2 filed on Jun. 29, 2001, which is hereby incorporated by reference in its entirety.

FIELD OF THE INVENTION

The invention relates to a method for identifying a compound which modifies the activity of the urotensin II receptor and thereby exerts an influence on aging processes in the coronary circulatory system.

BACKGROUND OF THE INVENTION

Urotensin II (UII) is a peptide which acts on blood vessels. It produces vasodilative or vasoconstrictive effects depending on the vessel type and on the species concerned. In many respects, its activity is comparable with that of angiotension II (AII). Urotensin II, as well as its receptor GPR14, are expressed in the human coronary circulatory system, for example in endothelial cells, smooth muscle cells of coronary arteries, the myocardium or the coronary atheroma. Both factors are therefore ascribed an important role in cardiovascular organization at the cellular level and consequently in pathophysiological processes. Urotensin II is known to be the natural ligand of GPR14. GPR14 is a member of the GPCR (G protein-coupled receptors) group.

The use of urotensin II in experiments performed on anesthetized monkeys led to dramatic changes in the hemodynamic parameters. The increase in the peripheral resistance, together with a weakening of cardiac contractility and a reduced cardiac output, led to the coronary circulatory system collapsing. Comparable events also take place in humans.

G protein-coupled receptors (GPCRs) play a central role in a large number of very different physiological processes. It is assumed that about 1000 genes in the human genome encode this family of receptors. Roughly 40-50% of the presently available pharmaceuticals which can only be obtained on prescription act as agonists or antagonists of GPCRs. This underlines the important role of this class of receptors for industry carrying out pharmacological research. Because of the size and importance of this protein family, and in view of the fact that the physiological ligands for many GPCRs are not yet known (orphan GPCRs), it must be assumed that this class of receptors will in future be one of the most important reservoirs for suitable target proteins when searching for novel pharmaceuticals.

GPCRs constitute a family of integral membrane proteins which are located on the surfaces of cells. They receive signals from extracellular signaling substances (e.g. hormones, neurotransmitters, peptides and lipids) and transmit these signals, by way of a family of guanine nucleotide-binding proteins, what are termed the G proteins, into the interior of the cell. In doing so, they activate a variety of signal transduction pathways depending on the specificity of the receptor, on the G protein which is activated and on the cell type.

The polypeptide chains of all GPCRs fold into seven $\alpha$ helices, which span the phospholipid double layer of the cell membrane. The seven transitions of the membrane give rise to extracellular and intracellular loops which make it possible to bind ligands extracellularly and to couple on G proteins intracellularly. For this reason, GPCRs are also termed seven-transmembrane receptors.

All G protein-coupled receptors function in accordance with a common basic pattern: the binding of an extracellular ligand leads to a change in the conformation of the receptor protein, thereby enabling the latter to make contact with a G protein. G Protein-mediated signal transduction cascades within the cell lead ultimately to the cell making a biological response.

G proteins are heterotrimeric proteins which are composed of the subunits $\alpha$, $\beta$ and (and, due to lipid anchors, are located on the inner side of the cell membrane. The coupling of activated GPCRs to G proteins brings about a GDP/GTP exchange on the G$\alpha$ subunit and the dissociation of the heterotrimer into an $\alpha$ subunit and a $\beta\gamma$ subunit. Both the activated $\alpha$ subunit and the $\beta\gamma$ complex are able to influence intracellular effector proteins.

Activation of the membrane-located adenylate cyclase (AC) by G proteins of the G$\alpha$s type leads, for example, to an increase in the intracellular level of cAMP, while activation by G proteins of the G$\alpha$i type leads to a fall in this level. G proteins of the Gq type activate phospholipase C (PLC), which catalyzes the formation of inositol 1,4,5-triphosphate (IP3) and diacylglycerol (DAG). These molecules in turn lead to $Ca^{2+}$ being released from intracellular stores or to protein kinase C (PKC) being activated, with further effects in both cases. In addition to the abovementioned G protein types (G$\alpha$i/s, Gq), still further types exist, with these types being designated G16, G12/13, etc. The multiplicity of these G proteins is reflected in the large number of very different functions possessed by GPCRs.

The mouse urotensin II receptor is disclosed in WO 00/75168. Methods for identifying agonists and antagonists for GPR14 are likewise disclosed, for example, in WO 99/40192.

The prior art with regard to screening methods has so far not yet taken any account of the fact that the urotensin II receptor can be used specifically for finding those compounds which are genes or gene products which are involved in the synthesis, structure or breakdown of the extracellular matrix. As a result, it is not possible to search effectively enough, from the pharmaceutical point of view, for substances which counteract diseases which are accompanied by an increase in connective tissue.

The citation of any reference herein should not be construed as an admission that such reference is available as "Prior Art" to the instant application.

SUMMARY OF THE INVENTION

The invention therefore relates to a method for identifying a compound which modifies the activity of the urotensin II receptor such that the activity or quantity of a gene or gene product which is involved in the structure, formation or breakdown of the extracellular matrix is influenced, by a] making available a cell in which a urotensin II receptor is formed, b] making available a chemical compound, c] bringing the cell from a] into contact with the chemical compound from b], d] determining the activity or quantity of a gene, or its gene product, from the cell from c], with this gene or gene product being involved in the structure, formation or breakdown of the extracellular matrix, e] comparing the activity or quantity from d] with the activity or quantity of the same gene or gene product from a corresponding control cell which has not been brought into contact with the compound from b].

The cell which is made available, and in which a urotensin II receptor is formed, is preferably the cell of a mammal, for example that of a mouse, a rat, a guinea pig or a hamster. Particular preference is given to a human cell being made available. In a particularly preferred embodiment, this cell is a heart cell.

The chemical compound which is made available for the method preferably has a molecular weight of between 100 and 50000 kDa, particularly preferably between 100 and 5000 kDa.

A chemical compound of this nature which is made available for the method is preferably a natural product, a protein, a polynucleotide, a sugar-containing compound or a fat-containing compound. Furthermore, this compound is preferably urotensin II.

The gene of the method according to the invention, or the corresponding gene product, whose activity or quantity is to be determined, is preferably the gene or gene product for Coll (collagen type 1), MMP2 (metalloproteinase type 2), TGFbeta (transforming growth factor beta) or CTGF (connective tissue growth factor).

The activity or quantity of the gene or gene product of the method according to the invention is preferably determined by means of quantitative PCR, by means of enzymic turnover or using antibodies.

The invention also relates to a pharmaceutical which comprises a compound which has been identified by a method according to the invention, as previously described. This pharmaceutical furthermore comprises substances which are required for formulating a pharmaceutical. This pharmaceutical is used for treating diseases of the coronary circulatory system.

In a preferred embodiment, the compound of this pharmaceutical has a molecular weight of from 100 to 50000 kDa. The molecular weight of this compound particularly preferably comes in the range between 100 and 5000 kDa.

This compound is preferably a natural product, a protein, a polynucleotide, a sugar-containing compound or a fat-containing compound. This compound can furthermore preferably be urotensin II.

The invention furthermore relates to the use of a compound, which has been identified by a method according to the invention, as previously described, for producing a pharmaceutical for treating diseases of the coronary circulatory system. In this connection, diseases of the coronary circulatory system are, for example, cardiac infarction, heart failure, decline in cardiac function in old age, a coronary vascular disease, pathological change in blood vessels, such as atherosclerosis, or angina pectoris. Those diseases of the coronary circulatory system which are connected with the formation of extracellular matrix, with it being possible for this formation to be pathologically altered, are particularly included. These diseases can be processes which particularly play a role in aging humans. In a preferred embodiment for using this compound, the compound has a molecular weight of between 100 and 50000 kDa, and in a particularly preferred embodiment, has a molecular weight of between 100 and 5000 kDa.

These and other aspects of the present invention will be better appreciated by reference to the following Detailed Description.

DETAILED DESCRIPTION OF THE INVENTION

Modification of the activity of a urotensin II receptor means that the signal transmission which is mediated by this receptor can be induced, increased, interrupted or attenuated. The activity of a urotensin II receptor is modified, in particular, by agonists or antagonists of urotensin II. However, the modification of the urotensin II receptor can also be effected using what are termed allosteric modulators. An agonist of urotensin II is a compound which supports, maintains or increases the effect of the urotensin II which naturally occurs in a particular cell, whereas an antagonist attenuates or abolishes this effect. An allosteric modulator of the urotensin II receptor can be a compound which itself has only low affinity for the receptor but which potentiates or inhibits the effect of agonists or antagonists. The activity or quantity of a gene or gene product is influenced when the activity or quantity of the gene or gene product concerned in a particular cell increases or decreases as compared with a control. The control then consists of a comparable cell which is not subjected to the measures which lead to this activity or quantity being influenced. In this connection, measures are understood, in particular, as being the bringing-into-contact of a compound with the cell. A cell in the above-mentioned sense can denote one or more cells of an organ or tissue of a vertebrate animal. Such cells can be derived from the brain, lung, muscle, fat tissue, connective tissue or the heart or from other organs. The cells can be present in the isolated state or still be present in the form of a tissue. These cells also include, in particular, cells from cell cultures. Examples of vertebrate animals are rats, mice, hamsters, guinea pigs and humans.

Urotensin II is a polypeptide. In humans, it consists of II amino acids. Urotensin II acts as a very effective vasoconstrictive hormone. In primates, it brings about systemic vascular constriction, contractile dysfunction of the myocardium and total circulatory collapse. The effect of urotensin II is mediated by way of the GPC receptor GPR14. Sequences for GPR14 have been disclosed. For example, the international application WO 00/75168 discloses the sequence of the mouse GPR14. Human recombinant urotensin II receptor is, for example, commercially available from "Euroscreen".

The extracellular matrix (ECM) plays a central role in maintaining the structural identity of tissues. ECM surrounds the tissue structures or individual cells. ECM is composed of collagens, noncollagenous glycoproteins and proteoglycans. Its composition varies in the different tissues. ECM forms a highly specialized, complex and dynamic network. In addition to its supporting function, it is involved, inter alia, in signal transmission, cell differentiation, adhesion, regeneration and migration. Furthermore, ECM plays an important role in the fibrosing of tissues, which should be understood as meaning an increased infiltration with connective tissue. This takes place, for example, in connection with scarring following injuries in the heart after a cardiac infarction, or in connection with fibrous changes in the lung or fibrous changes in the liver following intoxication of the liver with organic solvents or excessive and persistent alcoholism. Organs are also particularly affected by this fibrosing as the aging process advances, as a consequence of temporal events or as the result of excess stress. Functions which are defective in the formation of the extracellular matrix play an important role in fibrosis, in particular. Fibrosis is associated with excessively intensive scarring resulting from wound healing processes. Organs such as the heart, the kidneys, the liver, the lungs, the eyes or the skin may be affected. Fibrosis is characterized by an increased formation of collagen and loss of function in the affected organs.

Collagens, for example type I collagen or type IV collagen, laminins and other proteins are involved in the synthesis of the ECM. Proteinases which are to be counted as belonging to the metalloproteinase group, the serine proteinase group or the cysteine proteinase group play a role in the breakdown of the ECM.

Metalloproteinases possess characteristic functional domains. The signal sequence, the prodomain, the catalytic domain and the C-terminal hemopexin-like domain are conserved in the various members of the family. MMP2 and MMP9 contain additional fibronectin-like domains. MMP2 is also known as gelatinase A. Collagens I, II, IV, V, VII, X, XI and XIV, elastin, fibronectin, gelatin and laminin are substrates of MMP2. The TGFbeta signal pathway and the activation of CTGF are key processes for activating genes of extracellular matrix proteins such as collagen type I. CTGF is therefore also termed fibrogenic cytokine.

The provision of a cell comprises its preparation, culture and further processing. The provision is effected, for example, by preparing suitable cell material from organs or tissues or by propagating suitable cell lines or microorganisms. Various suitable nutrient media can be used for culturing. The cells are kept at a temperature which is optimal for the organism. Where appropriate, preservatives, antibiotics, pH indicators, blood serum constituents, blood serum, auxiliary substances, or other substances, are added to the particular growth medium employed. Methods for the preparation, culture and further processing are described in standard works (Example: Basic Cell Culture; Ed. J. M. Davis; IRL Press; 1994).

Preference is given to mammalian cells being suitable cells. These cells can comprise primary cells or cell lines. Examples of such cells are primary cells from mammalian organs (e.g. brain, muscle, fat tissue, connective tissue, heart, lung, liver, kidney, blood vessels, hormone glands, and others). The cells can be nerve cells, muscle cells, fat cells, fibroblasts, leukocytes, lung cells, liver cells, kidney cells or other types of cells. Suitable cell lines are, preferably, CHO, HEK 293, COS, mouse 3T3 or hela cells, or other types of cell. Preference is also given to the possibility of using yeast cells.

A chemical compound is made available, in particular, by chemical synthesis or by isolating chemical substances from biological material. Biological material contains living or nonliving cells, or constituents of these cells.

For synthesizing a compound chemically, or for isolating a substance from biological cells, the skilled person can have recourse to routine methods. These methods are available to the skilled person in textbooks such as "Organic Synthesis Workbook; 1995; John Wiley & Sons; ISBN 3-527-30187-9", "The Organic Chemistry of Drug Synthesis; 1998; John Wiley & Sons; ISBN 0-471-24510-0" or "Bioactive Compounds from Natural Sources; 2001; Taylor & Francis; ISBN 0-7484-0890-8". The compounds which have been obtained by synthesis or isolation can be brought into solution in a suitable solvent. Suitable solvents can contain water, buffering substances (e.g. Tris, Hepes, Mops, and others), monovalent and/or divalent ions (e.g. $K^+$, $Na^+$, $Mg^{2+}$, $Ca^{2+}$ and others), acids (e.g. HCl, $H_2SO_4$, formic acid, acetic acid, and others), caustic alkalis (e.g. NaOH, and others), alcohol (e.g. methanol, ethanol and glycerol), detergents (e.g. Na dodecyl sulfate, and others), organic solvents (e.g. formamide, acetone, dimethyl sulfoxide, and others), and also other constituents, in particular for solubilization or stabilization. A chemical compound for the method according to the invention should be suitable for use as a ligand for a GPCR.

A compound of this nature can, in particular, be obtained from the tissues or organs of vertebrates, such as endothelial cell tissue, heart tissue, brain tissue, blood, serum or plasma.

The skilled person can use routine methods from the laboratory for bringing the chemical compound into contact with said cell line. The bringing-into-contact is effected, for example, in Erlenmayer flasks, test tubes or Eppendorf tubes or on microtiter plates. For the bringing-into-contact, it is possible to use thermostatted incubators in which it is possible to set a constant temperature of, for example, 30° C. or 37° C. and also uniform $CO_2$ conditions or atmospheric humidity conditions. The bringing-into-contact can, in particular, also be effected in appliances, which are designated for this purpose, in a laboratory robot. It is possible for the bringing-into-contact to take place over different periods of time, extending from a few seconds, by way of minutes, up to several hours. The conditions which are in each case to be selected depend on the receptor, the cell line and the chemical compound.

The activity or quantity of a gene or its gene product can refer to the activity of the gene with regard to its promoter, to the quantity of RNA and mRNA which is formed and to the enzymic activity or quantity of the protein which is encoded by the gene. Different methods, such as PCR or hybridization techniques, can be used for determining the quantity of an mRNA in a cell. PCR techniques which are available to the skilled person, in particular, are the real-time PCR systems which are marketed commercially by various suppliers. Examples of these suppliers are Applied Biosystems, Bio-Rad, Cepheid, Cortett Research, Roche Molecular Biochemicals and Stratagene. Real-time PCR systems belong to the skilled person's tools of the trade. Examples of suitable hybridization techniques for determining the quantity of RNA are dot blot hybridization and Northern hybridization. Both techniques make use of the formation, which is brought about by base pairing, of a double-stranded nucleic acid molecule from two separate single strands, with one of the strands being fixed on a support surface and the other, mobile strand possessing a label, of radioactive or other nature, which can be detected relatively simply. The skilled person is familiar with hybridization techniques. He can find them in standard manuals such as, in particular, "Current Protocols in Molecular Biology; edited by Fred M. Ausubel, Roger Brent, Robert E. Kingston, David D. Moore, J. G. Seidman, John A. Smith, Keven Struhl; John Wiley & Sons, Inc., New York, 2001.

The activity or quantity of a protein can be determined by way of its enzymic activity or using specific antibodies. In the case of the enzymic activity, the turnover of the particular enzyme with regard to its substrate is determined. This involves setting up an assay which ensures optimal activity conditions for the enzyme with regard to pH, cofactors, ionic milieu, temperature and substrate concentration, and enables a measurement to be made within the range which is proportional to turnover. The substrate turnover can be determined, for example, by incorporating radioactively labeled precursors into macromolecules or fragmenting radioactively labeled macromolecules into breakdown products, subsequently separating the breakdown products and determining the respective radioactive quantity. When antibodies are used for determining the quantity of a protein, the skilled person makes use of techniques such as Southern hybridization, RIA (radioimmunoassay), ELISA (enzyme-linked immunosorbent assay), and others.

The skilled person will also find detailed practical instructions for carrying out these detection methods in the previously mentioned "Current Protocols in Molecular Biology".

In the pharmaceutical, the compound is preferably present, together with a tolerated excipient, in the form of a pharmaceutical composition. The excipient has, of course, to be well tolerated in the sense that it is compatible with the other constituents in the composition and is not harmful to the health of the patient. The excipient can be a solid or a liquid or both and is preferably formulated with the compound as a single dose, for example as a tablet, which can comprise from 0.05% to 95% by weight of the active compound.

The pharmaceutical compositions according to the invention can be produced by any of the known pharmaceutical methods which essentially comprise mixing the constituents with pharmacologically tolerated carrier substances and/or auxiliary substances. Pharmaceutical compositions according to the invention are those which are suitable for oral, rectal, topical, peroral (e.g. sublingual) and parenteral (e.g. subcutaneous, intramuscular, intradermal or intravenous) administrations.

The quantity of a compound which is required for achieving a desired biological effect depends on a number of factors such as the specific compound which is selected, the intended use, the type of administration and the clinical status of the patient. Quantity data which are mentioned below relate to a ligand.

In general, the daily dose is in the range of from 0.3 mg to 100 mg (typically of from 3 mg to 50 mg) per day and per kilogram of body weight, e.g. 3-10 mg/kg/day. An intravenous dose can, for example, be in the range from 0.3 mg to 1.0 mg/kg, which dose can suitably be administered as an infusion of from 10 ng to 100 ng per kilogram per minute. Suitable infusion solutions for these purposes can, for example, contain from 0.1 ng to 10 mg, typically from 1 ng to 10 mg, per milliliter. Single doses can contain, for example, from 1 mg to 10 g of the active compound. Consequently, ampoules for injections can contain, for example, from 1 mg to 100 mg, while single dose formulations which are administered orally, such as tablets or capsules, can contain, for example, from 1.0 to 1000 mg, typically from 10 to 600 mg.

Abbreviations

| | |
|---|---|
| AII | angiotensin II |
| ColI | collagenase I |
| Con | control |
| MMP2 | matrix metalloproteinase II |
| UII | urotensin II. |

The present invention may be better understood by reference to the following non-limiting Examples, which are provided as exemplary of the invention. The following Examples are presented in order to more fully illustrate the preferred embodiments of the invention. They should in no way be construed, however, as limiting the broad scope of the invention.

EXAMPLES

1. Isolating and Culturing Fibroblasts from Human Hearts

Fibroblasts were isolated from human hearts as described in Cell and Tissue Research 286, 145-153 (1996). 96-98% of the resulting cell culture consisted of fibroblasts.

For the purpose of implementing this procedure, heart tissue was cut into small pieces and incubated three times, at 37° C. for 20 minutes, in KHB (Krebs Henseleit buffer) containing 2 mg of collagenase/ml and 2 mg of dispase/ml. The homogenates were combined and then centrifuged. The sediments were taken up in 10 ml of KHB. The cells were added, in portions of in each case 2 to 3 ml, to uncoated plastic containers. The volume was made up to 10 ml with DMEM (Dulbecco's modification of Eagle's medium) containing 4.5 mg of glucose/l and 10% FCS (fetal calf serum). After having been incubated at 37° C. for 1 hour, the cells were washed twice with PBS (phosphate-buffered saline) and subsequently cultured, at 37° C. and 5% $CO_2$, for approx. 4-8 weeks until 90% confluence had been reached. There then followed two further passages of in each case 4 weeks' duration. The cells employed in the present experiments were used after the second passage and at 70% to 90% confluence (approx. 3 months after isolation).

2. Stimulating Fibroblasts from Human Hearts with Angiotensin II and Urotensin II The reagents for implementing the cell culture techniques were obtained from Gibco BRL Life Technologies. The cells were first of all kept, at 37° C., in serum-free DMEM containing 4000 mg of glucose/l, 2 mM L-glutamine, 100 μg/0.1 mg of penicillin/streptomycin/ml and 0.1% BSA (bovine serum albumin) before angiotensin II or urotensin II was added, in each case up to a final concentration of 0.1 μM. RNA was then prepared from the cells after 6 hours.

3. Using Real-time PCR to Quantify Specific RNAs

The RNA was isolated by means of standard methods using guanidinium chloride.

Reverse transcriptase (10 units/ng of RNA) was used to transcribe 500 ng of the RNA from each sample into DNA. For degrading the DNA, the entire volume, containing approx. 8-10 μg of RNA, was incubated with DNase I.

The RNAs were quantified using a LightCycler and a Fast Start SYBR Green RT-PCR kit supplied by Roche Molecular Biochemicals. Corresponding kits from other companies such as Applied Biosystems, Bio-Rad or Stratagene are also suitable for the same purpose. The primers corresponding to SEQ ID No. 1 and 2 were used as primers for Col I, while the primers corresponding to SEQ ID No. 3 and 4 were used as primers for MMP2, the primers corresponding to SEQ ID No. 5 and 6 were used as primers for GAPDH, as the control, the primers corresponding to SEQ ID No. 7 and 8 were used as primers for TGFbeta, and the primers corresponding to SEQ ID No. 9 and 10 were used as primers for CTGF. The reaction was first of all kept constant at 95° C. for 10 min. There then followed 40 cycles, with each cycle comprising an incubation for 10 sec at 95° C., 5 sec at 60° C. and 12 sec at 72° C. A melting curve was used to confirm the specificity of the reaction. The quantities were equalized using GAPDH mRNA as the control.

4. Inducing Genes which are Involved in Synthesizing the Basement Membrane in Heart Fibroblasts Fibroblasts were isolated from three human hearts and used in the first passage. The cells were cultured up to approx. 80% confluence, kept for a further 24 hours without serum and stimulated for 6 hours, in each case in duplicate assays, with 1 μM urotensin II, 1 μM angiotensin II or buffer substances as controls. The mRNAs (collagen 1, matrix metalloproteinase 2, TGFbeta1 and CTGF) were quantified by real-time PCR using a LightCycler™. The GAPDH (glyceraldehyde-3-phosphate dehydrogenase) mRNA was used as the standard reference. Real-time PCR (polymerase chain reaction in real time) makes it possible to determine specific nucleic acids quantitatively. The technique is based on using fluorescent dyes in combination with the polymerase chain reaction of reverse-transcribed RNA. Different suppliers of assay kits now exist. For example, the system can be obtained commercially from Applied Biosystems, Bio-Rad, Cepheid, Carbett Research, Roche Molecular Biochemicals or Stratagene.

Stimulation with urotensin II led to significant increases in the mRNAs for collagen I, MMP2, TGFbeta1 and CTGF

|     | Col 1        | MMP 2        | TGFbeta1      | CTGF          |
| --- | ------------ | ------------ | ------------- | ------------- |
| Con | 0.56 +/− 0.1 | 0.43 +/− 0.2 | 0.60 +/− 0.09 | 0.45 +/− 0.27 |
| UII | 0.92 +/− 0.3* | 0.65 +/− 0.3* | 0.81 +/− 0.1* | 0.88*/−0.2*  |
| AII | 0.56 +/− 0.27 | 0.22 +/− 0.1 | 0.71 +/− 0.07 | 0.34 +/− 0.9  |

*$p < 0.05$ vs control;

The formation of these RNAs demonstrates the enormous importance of urotensin II and its receptor for matrix synthesis and tissue remodeling in vessels and in the heart. Corresponding agonists and antagonists are therefore of great pharmacological value with regard to restructuring in the heart, in particular following a heart attack in the regions affected, for the purpose of avoiding, preventing or reversing the siccatrization of the heart tissue, or slowing down the development of cardiac failure or cardiac insufficiency, and also, in particular, in association with high blood pressure or obstructive lung diseases. Angiotensin II is the main effector molecule of the renin-angiotensin system. The peptide hormone brings about a variety of physiological effects. Thus, angiotensin II is involved in changing peripheral resistance. It exerts an effect on kidney function and regulates sodium reabsorption, inter alia. In addition to this, it acts as a growth factor.

5. Using Urotensin to Induce Collagen Synthesis in Human Cardiac Fibroblasts

Human cardiac fibroblasts were isolated from seven explanted human hearts in the terminal stage of cardiac insufficiency due to dilated cardiomyopathy. Four cell preparations were also made from healthy donor hearts. The fibroblasts were isolated in sterile 10 cm Petri dishes and cultured as previously described. After about 12 weeks of culturing, the cells reached the second passage with a confluence of approx. 80%. At this stage, the serum was withdrawn for 48 hours and the cells were subsequently stimulated for various intervals of time (between 6 and 24 hours) with UII, Ang II, TNFalpha, TGFβ, UII+TNFa, (in each case $10^{-7}$ mol/l), or buffer (control). The determinations were carried out in duplicate or in triplicate. After the stimulation, the cells were washed, removed from the Petri dishes with 1 ml of PBS and centrifuged down in Eppendorf tubes (100 rpm, 5 min, 4° C.). The supernatant was discarded. 100 ul of lysis buffer (Nonidet P40, 0.5%, SDS 0.5%) were added to about 50 ul of cells and the mixture was incubated on ice for a further 20 minutes. The lysate was centrifuged once again (20 minutes, 1400 rpm, 4° C.) and the supernatant was used for the subsequent experiments. Protein was determined by means of the BCA (bicinchoninic acid) assay. The homogenates were diluted down to a protein concentration of 2 ug/ul.

Procollagen type I C-peptide in the fibroblasts from all the hearts was determined on a 96-well microtiter plate using a commercially obtainable solid-phase ELISA assay (TaKaRa Biomedicals, Shuzo Co, Ltd.). The assay was carried out in accordance with the manufacturer's instructions. When this was done, no crossreactivity was seen with human fibronectin, vitronectin, laminin, collagen type I or collagen type III. The values for the procollagen type I C-peptide were determined using a standard curve of 10-640 ng/ml. The standards were provided by the manufacturer. The absorption values for the stimulations obtained with the controls (buffer) were set at 100%. The absorption values for the stimulated cells were related to the control values obtained for the same heart. In each case, the mean values from duplicate or triplicate determinations were used for the calculations. A bilateral, unpaired t test was used for statistically evaluating the comparison of the stimulation responses in control cells and in cardiac insufficiency cells.

In the explanted heart fibroblasts from the hearts suffering from heart failure, procollagen I protein is increased following stimulation with UII (173+/−42% of the control), Ang II (205+/−67%) and TGF β (202+/−52%), and, to a lesser extent, with TNFalpha (139+/−26%) (table 1). While the increase was time-dependent, it was already observed after 6 hours. By contrast, the quantity of collagen protein was not changed in the donor heart fibroblasts which had been stimulated with the same peptides: UII (98% of the control), Ang II (88%), TGFβ (97%) and TNFalpha (86%). The differences between the cells in the control hearts and the cells from the hearts suffering from cardiac insufficiency were statistically significant following stimulation with UII and TNFalpha. The same tendencies were also observed when AngII and TGFbeta were used.

TABLE 1

| Heart (No.) | Time (hrs.) | Contr. | Ang II | TGFβ | UII | TNFa | UII + TNF |
| --- | --- | --- | --- | --- | --- | --- | --- |
|  |  | (Absorption, in % of the controls) | | | | | |
| Collagen synthesis in fibroblasts derived from hearts in the terminal stage of cardiac insufficiency (EFH) | | | | | | | |
| 1  | 24 h | 100 | 142 | 166 | 198 | 166 |     |
| 4  | 24 h | 100 | 471 | 377 | 458 | 262 |     |
| 10 | 5 h  | 100 | 94  | 142 | 102 | 67  |     |
| 11 | 5 h  | 100 | 113 | 123 | 243 | 91  |     |
| 12 | 12 h | 100 | —   | —   | 117 | 107 | 128 |
| 13 | 12 h | 100 | —   | —   | 165 | 126 | 139 |
| 14 | 12 h | 100 | —   | —   | 226 | 190 | 218 |
| MV |      | 100 | 205 | 202 | 173 | 139 | 162 |
| SEM |     |     | 67  | 52  | 42  | 26  | 18  |
| Collagen synthesis in control hearts (contr.) | | | | | | | |
| 3 | 6 h  | 100 | 84  | 84  | 103 | 81  |     |
| 3 | 12 h | 100 | 92  | 123 | 80  | 92  |     |
| 5 | 6 h  | 100 | 88  | 71  | 106 | 77  |     |
| 6 | 6 h  | 100 | —   | 110 | 104 | 92  |     |
| MV |     | 100 | 88  | 97  | 98  | 86  |     |
| SEM |    |     | 2   | 12  | 6   | 4   |     |
| p (EFH versus controls) | | | 0.3 | 0.16 | 0.05 | 0.02 | |

(No.): internal code number for the hearts.

The present invention is not to be limited in scope by the specific embodiments describe herein. Indeed, various modifications of the invention in addition to those described herein will become apparent to those skilled in the art from the foregoing. Such modifications are intended to fall within the scope of the appended claims.

It is further to be understood that all base sizes or amino acid sizes, and all molecular weight or molecular mass values set forth in the instant specification and claims are approximate, and are provided for description.

Various publications are cited herein, the disclosures of which are incorporated by reference in their entireties.

The invention claimed is:

1. A method for identifying a compound that modifies the activity of urotensin II receptor resulting in a change in activity of a gene or activity or quantity of a gene product comprising:
   a] providing a cell in which urotensin II receptor is expressed,
   b] providing said compound,
   c] contacting said cell from a] with said compound from b],
   d] measuring the activity of the gene or activity or quantity of a gene product wherein the gene or the gene product is selected from the group consisting of metalloproteinase type 2 (MMP2,), transforming growth factor beta 1 (TGFβ1) and connective tissue growth factor (CTGF),
   e] measuring the activity of the gene or activity or quantity of a gene product from a control cell not contacted with said compound, and
   f] comparing the measurement from d] and e] wherein a difference obtained from f] identifies said compound as changing the activity of the gene or activity or quantity of a gene product resulting from modification of urotensin II receptor activity.

2. The method of claim 1, wherein said cell is an isolated mammalian cell.

3. The method of claim 2, wherein said cell is an isolated human cell.

4. The method of claim 2, wherein said isolated cell is a heart fibroblast cell.

5. The method of claim 1, wherein said compound is a natural product, a protein, a polynucleotide, a sugar-containing compound or a fat-containing compound.

6. The method of claim 5, wherein said compound is urotensin II.

7. The method of claim 1, wherein the gene or gene product is measured using-quantitative PCR, a detectable antibody or by enzymatic turnover of a detectable substrate.

8. The method of claim 1 wherein the difference obtained in f] indicates an increase in the activity of the gene or activity or quanitity of a gene product of, MMP2, TGFβ1 and CTGF compared to the control cell.

\* \* \* \* \*

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
cgttggacct cctggtaatc                                                    20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ccttgttacc gctctctcct                                                    20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
acctggatgc cgtcgtggac                                                    20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tgtggcagca ccagggcagc                                                    20

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
gcaggaggca ttgctgat                                                      18

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
caccatcttc caggagcgag                                                    20

<210> SEQ ID NO 7
<211> LENGTH: 20

```
<212> TYPE: DNA
<213> ORGANISM: Artificial Sequence
<220> FEATURE:
<223> OTHER INFORMATION: primer

<400> SEQUENCE: 7
gttgtaatgg caggcacagg                                          20

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
cacactgcaa gtggacatca acg                                      23

<210> SEQ ID NO 9
<211> LENGTH: 24
<212> TYPE: DNA
<213> ORGANISM: Artificial Sequence
<220> FEATURE:
<223> OTHER INFORMATION: primer

<400> SEQUENCE: 9
tctccgtgga gctgaagcaa tagt                                     24

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggcttaccga ctggaagaca                                          20
```